United States Patent [19]

Ohsaka et al.

[11] Patent Number: 5,166,365
[45] Date of Patent: Nov. 24, 1992

[54] FLUORINE-CONTAINING AROMATIC COMPOUND, PROCESS FOR PREPARING THE SAME AND USE THEREOF

[75] Inventors: Yohnosuke Ohsaka, Ibaraki; Tsutomu Kobayashhi, Settsu; Motonobu Kubo, Toyonaka, all of Japan

[73] Assignee: Daikin Industries Ltd., Osaka, Japan

[21] Appl. No.: 521,449

[22] Filed: May 10, 1990

Related U.S. Application Data

[62] Division of Ser. No. 177,446, Apr. 4, 1988, Pat. No. 4,946,935.

[30] Foreign Application Priority Data

Apr. 3, 1987 [JP] Japan ................................. 62-82592
Apr. 20, 1987 [JP] Japan ................................. 62-97013
Jul. 30, 1987 [JP] Japan ................................. 62-191323
Jan. 12, 1988 [JP] Japan ................................. 63-4500

[51] Int. Cl.$^5$ ................................. C07D 407/06; C07D 407/12
[52] U.S. Cl. ................................. 549/241; 549/466; 549/472; 560/190; 562/468; 562/474; 564/315; 564/323; 568/314; 568/332; 568/611; 568/660; 568/661; 570/144
[58] Field of Search ................................. 549/241, 466, 472; 560/190; 562/468, 474; 564/315, 323; 568/314, 332, 611, 660, 661; 570/144

[56] References Cited

U.S. PATENT DOCUMENTS 4,885,116 12/1989 Alston et al. ................................. 549/241

Primary Examiner—C. Warren Ivy
Assistant Examiner—Ba K. Trinh
Attorney, Agent, or Firm—Birch, Stewart, Kolasch & Birch

[57] ABSTRACT

A novel fluorine-containing aromatic compound of the formula:

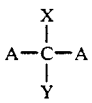

wherein X is $$-(CH_2)_p(CHF)_q(CFO)_r(CFCF_2O)_s(CF_2CF_2CF_2O)_tR_f'$$

with $R_f$ substituents on the CFO and CFCF$_2$O units in which
$R_f$ is a perfluoroalkyl group having 1 to 10 carbon atoms,
$R_f'$ is a perfluoroalkyl group having 1 to 12 carbon atoms,
p is an integer of 1 to 3,
q is an integer of 0 to 3,
r is 0 or 1,
s is an integer of 0 to 5
and t is an integer of 0 to 5,
Y is X, a hydrogen atom, an alkyl group having 1 to 8 carbon atoms or a fluoroalkyl group having 1 to 8 carbon atoms, and
each A is independently

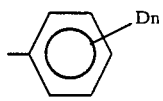

in which D is an amino, carboxyl, hydroxyl, methyl or haloformyl group, and n is an integer of 1 or 2, or

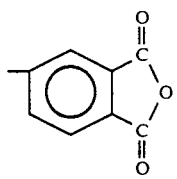

can be used to derive various compounds, some of which are useful for preparing a fluorine-containing epoxy compound of polyimide with good properties.

2 Claims, No Drawings

FLUORINE-CONTAINING AROMATIC COMPOUND, PROCESS FOR PREPARING THE SAME AND USE THEREOF

This application is a divisional of copending application Ser. No. 07/177,446 filed on Apr. 4, 1988, now U.S. Pat. No. 4,9446,935.

BACKGROUND OF THE INVENTION

1. Field of the Invention

The present invention relates to a fluorine-containing aromatic compound, a process for preparing the same and use thereof.

2. Description of the Related Art

Some aromatic compounds comprising two benzene rings and two trifluoromethyl groups are known. For example, U.S. Pat. No. 3,959,350 discloses a compound of the formula:

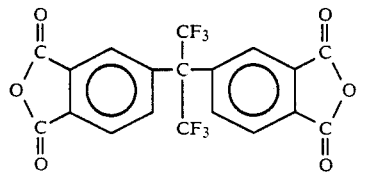

(1)

J. Polym. Sci., B-3, 1021 (1965) discloses a compound of the formula:

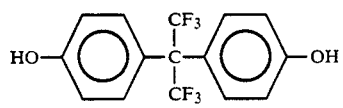

(2)

These known compounds are useful as starting materials in the production of fluorine-containing epoxy resins and fluorine-containing polyimides.

However, a compound of the formula (1) or (2) in which at least one of the trifluoromethyl groups is replaced with a perfluoroalkyl group having at least two carbon atoms has not been known. This may be because replacement of trifluoromethyl group with the perfluoroalkyl group having at least two carbon atoms is very difficult due to steric hindrance.

Hitherto, as a fluorine-containing epoxy resin, a polymer of an epoxide of the formula:

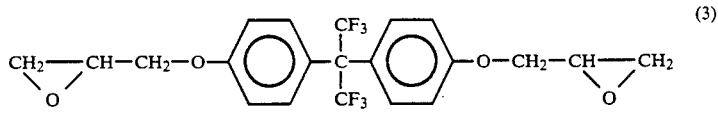

(3)

is known (cf. J. Polym. Sci., B-3, 1021 (1965)). The cured product of this polymer has a refractive index $n_D^{23}$ of 1.524 to 1.527. When an epoxy resin is used as an adhesive for a quartz optical fiber, it is advantageous that the adhesive has a refractive index as close as possible to that of the quartz ($n_D^{23} = 1.46$). Therefore, the epoxy resin (3) is not satisfactory as an adhesive for optical parts or elements such as the quartz optical fiber and an optical connector.

Polyimide resins are known to have good heat resistance and electric insulation property, and used as flexible substrates for printed circuits, a protective coating for various elements, an adhesive for bonding a chip to a substrate and the like. However, the conventional polyimide is highly hygroscopic. Therefore, it causes corrosion in these applications and its adhesiveness decreases. To improve the hygroscopicity of polyimide, fluorine-containing polyimides comprising repeating units of the following formula are proposed:

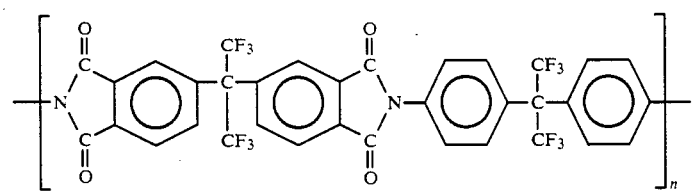

(4)

(Japanese Patent Publication No. 1876/1968) and

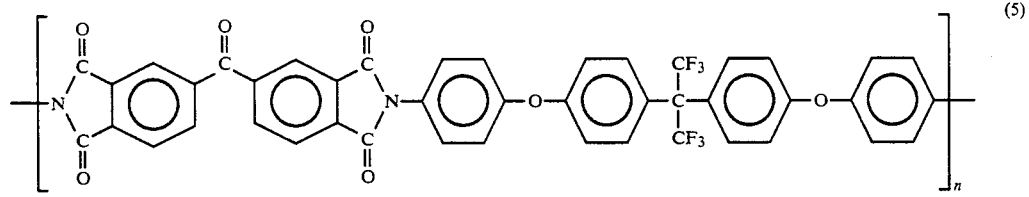

(5)

(Ales Transaction, 27, 189 (1984)).

Although these fluorine-containing polyimides have less hygroscopicity than the conventional polyimides, they still absorb about 0.5 to 1.0% of water. Therefore, a polyimide having much less hygroscopicity has been desired.

In order to improve moisture resistance of a semiconductor device and to prevent software errors caused by alpha-ray, it is known to provide a protective coating of a polyimide resin on a surface of the semiconductor device. Also, a semiconductor device having multilayer wiring in which the polyimide layer is provided between the adjacent layers is known. However, as described above, since the conventional polyimide has large hygroscopicity, the device tends to be corroded or adhesiveness is deteriorated. Practically, the corrosion or the deterioration of adhesiveness results in corrosion breaking of an aluminum or copper wire used for wiring of LSI, blister of an insulating layer by abrupt heating during soldering or in a bonding step, and leakage current in case where the polyimide is used as a surface stabilizing layer on an exposed end of PN junction. Then, it has been proposed to use a fluorine-containing polyimide having improved hygroscopicity as a protective film for the semiconductor device. For example, Japanese Patent Kokai Publication No. 177659/1985 discloses a method for producing a semiconductor device comprising applying a polyamic acid which is prepared by reacting dianhydride of a tetracarboxylic acid of the formula:

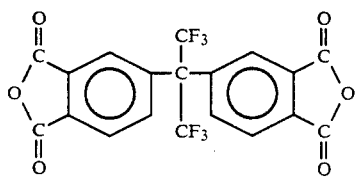

and a diamine of the formula:

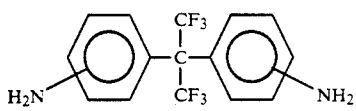

and then curing the polyamic acid.

By the above method, the hygroscopicity is not satisfactory and the problems caused by hygroscopicity are not solved.

SUMMARY OF THE INVENTION

One object of the present invention is to provide a novel fluorine-containing aromatic compound comprising at least one substituent having a perfluoroalkyl group of two or more carbon atoms, which substituent is bonded to a carbon atom to which two benzene rings are bonded.

Another object of the present invention is to provide a fluorine-containing epoxy resin which is useful as an adhesive for optical parts such as quartz optical fibers and optical connectors.

A further object of the present invention is to provide a fluorine-containing polyimide having less hygroscopicity than the conventional polyimides and improved heat resistance.

A yet another object of the present invention is to provide a semiconductor device which has high moisture resistance and can overcome the problems which are found in the conventional semiconductor device.

DETAILED DESCRIPTION OF THE INVENTION

A novel fluorine-containing aromatic compound of the present invention is represented by the formula:

  (I)

wherein X is

in which $R_f$ is a perfluoroalkyl group having 1 to 10 carbon atoms, $R_f'$ is a perfluoroalkyl group having 1 to 12 carbon atoms, p is an integer of 1 to 3, q is an integer of 0 to 3, r is 0 or 1, s is an integer of 0 to 5 and t is an integer of 0 to 5,

Y is X, a hydrogen atom, an alkyl group having 1 to 8 carbon atoms or a fluoroalkyl group having 1 to 8 carbon atoms, and each A is independently

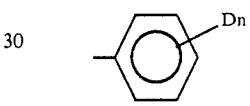

in which D is an amino, carboxyl, hydroxyl, methyl or haloformyl group and n is integer of 1 or 2, or

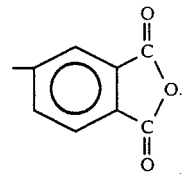

Among the novel fluorine-containing aromatic compound (I) of the present invention, that having a methyl group(s) or a hydroxy group(s) on the benzene ring may be prepared by reacting a compound of the formula:

XCOY  (II)

wherein X and Y are the same as defined above with a compound of the formula

A-H  (III)

wherein A is the same as defined above in the presence of a Lewis acid.

Specific examples of the compound (II) are:

$C_8F_{17}CH_2CH_2COCF_3$
$C_3F_7OC(CF_3)FCH_2CH_2COCF_3$
$C_4F_9CH_2CH_2COCF_3$
$C_8F_{17}CH_2CH_2COH$
$C_8F_{17}CH_2CH_2COCH_2CH_2CF_2CF_2(OCF_2CF_2CF_2)_nF$ (n is 1 to 5)
$H(CF_2CF_2)_3CH_2CH_2COCF_3$
$H(CF_2CF_2)CH_2CH_2COCH_2CH_2C_8F_{17}$

Specific examples of the compound (III) are toluene, o-xylene, phenol and catechol.

Since the reaction of the compounds (II) and (III) is an electrophilic substitution, any compound having an electron-donor group can be used as the compound (III). By an analogous reaction, an aromatic compound having an electron-donor group or no substituent may be prepared.

The compound (II) may be prepared by a Grignard reaction according to the following reaction formula:

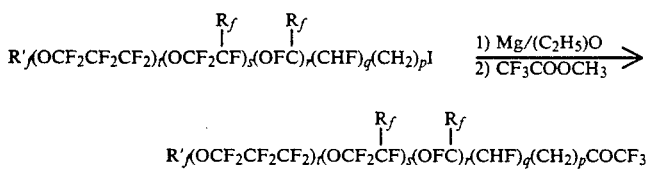

wherein $R_f$, $R_f'$, p, q, r, s and t are the same as defined above.

Preferably, two or more equivalents of the compound (III) is reacted with one equivalent of the compound (II).

The reaction is carried out in the presence of a Lewis acid. Examples of the Lewis acid are hydrogen fluoride, aluminum chloride, iron (III) chloride, zinc chloride, boron trifluoride, $HSbF_6$, $HAsF_6$, $HPF_6$, $HBF_4$, etc. Among them, hydrogen fluoride is preferred.

An amount of the Lewis acid to be used is from 15 to 100 moles, preferably 20 to 50 moles per mole of the compound (II).

The reaction is preferably carried out in the presence of a solvent. Examples of the solvent are dimethylformamide (DMF), hexamethylphosphoramide (HMPA), dimethylacetoamide (DMAc), N-methylpyrolidone, 1,1,2,2-tetrachloro-1,2-difluoroethane, dimethylsulfoxide (DMSO), tetrahydrofuran (THF) and the like. Hydrogen fluoride used as the Lewis acid may act as a solvent.

The reaction temperature is usually from 50° to 200° C., preferably from 70° to 150° C. The reaction pressure is usually from 5 to 20 kg/cm², preferably from 7 to 15 kg/cm². The reaction time varies with other reaction conditions such as the reaction temperature, and is usually from 1 to 24 hours.

The reaction product may be recovered from the reaction mixture by a per se conventional method. For example, the reaction product is extracted with a suitable solvent such as trichlorotrifluoroethane and chloroform and the solvent is evaporated off from the extract to leave the reaction product.

Among the novel fluorine-containing aromatic compound (I) of the present invention, one having carboxyl groups on the benzene rings can be prepared by oxidizing the compound of formula:

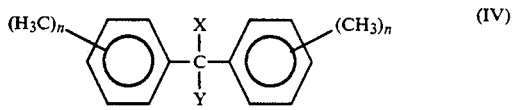

wherein X, Y and n are the same as defined above, which is prepared by the above reaction.

The oxidation can be effected by a per se known oxidizing agent such as nitric acid, nitrous acid, chromic acid, permanganic acid, chloric acid, etc. The oxidation is preferably effected at a temperature of 140° to 200° C., more preferably from 170° to 190° C. for 0.5 to 10 hours, preferably for 2 to 4 hours.

Among the novel fluorine-containing aromatic compound (I) of the present invention, one having amino groups on the benzene rings can be prepared by reacting a compound of the formula:

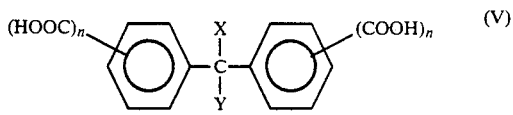

wherein X, Y and n are the same as defined above with hydrazoic acid in the presence of a strong acid.

An amount of hydrazoic acid to be used is 1 to 2 moles per mole of the compound (V).

Examples of the strong acid are sulfuric acid, hydrochloric acid, nitric acid, etc. An amount of the strong acid is 20 to 50 equivalents per equivalent of the compound (V).

This reaction is carried out at a temperature of 40° to 60° C., preferably 50° to 60° C. for 1 to 10 hours, preferably for 2 to 4 hours. Preferably, the reaction is carried out in the presence of a solvent such as chloroform.

Among the novel fluorine-containing aromatic compound (I) of the present invention, an anhydride of the formula:

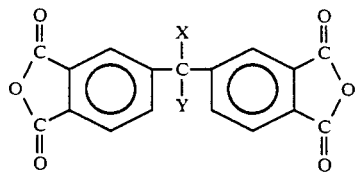

wherein X and Y are the same as defined above is prepared by dehydrating the tetracarboxylic acid of the formula:

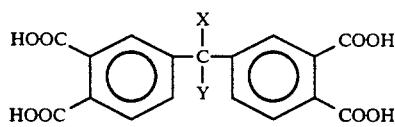

wherein X and Y are the same as defined above which is prepared by the above described process.

This dehydration is effected, under reduced pressure or in a stream of nitrogen gas, at a temperature of 100° to 200° C., preferably 140° to 180° C. When the reduced pressure is applied, a pressure is from 10 to 200 mmHg, preferably from 20 to 100 mmHg. The dehydration may be carried out in the presence of a solvent. In such case, a solution of the above tetracarboxylic acid is heated up to a boiling point of the solvent. Examples of the solvent are toluene, xylene, chlorobenzene, n-octane, 1,1,1,2-tetrachloroethane, 1,1,2,2-teterachloroethane and the like.

Among the novel fluorine-containing aromatic compound (I) of the present invention, one having the chloroformyl groups on the benzene rings can be prepared by reacting the compound (V) with phosphorus pentachloride, phosphorus trichloride or thionyl chloride. In this reaction, the chlorinating agent is used in an amount equal to or more than equivalent. The reaction is carried out while cooling since it is an exothermic reaction, although it may be carried out while heating. The reaction is carried out in the absence or presence of a solvent. Examples of the solvent are chloroform, benzene, petroleum ether and the like. The reaction product can be recovered by rectification.

Among the novel fluorine-containing aromatic compound (I) of the present invention, one having the bromoformyl groups on the benzene rings can be prepared by reacting the compound (V) with phosphorus pentabromide or phosphorus tribromide. The reaction conditions are substantially the same as in the preparation of the compound (I) having the chloroformyl groups.

The novel fluorine-containing aromatic compound (I) of the present invention is useful as a monomer of various polymers. By polymerizing the compound (I), polyamide, polyimide, polyarylate, epoxy resin, polyester, polycarbonate and the like can be produced according to the kinds of the substituents. Since the polymer comprising the compound (I) has a large fluorine content, they have good weather resistance and low hygroscopicity.

From the novel fluorine-containing aromatic compound (I), a novel fluorine-containing epoxy compound is produced. The novel fluorine-containing epoxy compound is represented by the formula:

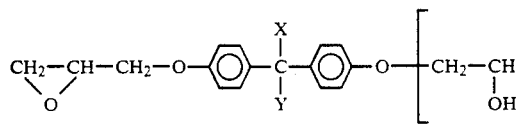

wherein X and Y are the same as defined above and n is a number of 0 to 30.

The epoxy compound may be a liquid or solid depending on a polymerization degree.

The novel epoxy resin of the present invention can be prepared by reacting a phenol compound of the formula:

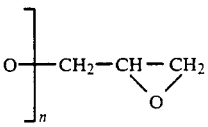 (VI)

wherein X and Y are the same as defined above with epichlorohydrin.

The compound (VI) is prepared by reacting the compound (II) with a phenol.

In the former reaction, epichlorohydrin is used in an amount of 10 to 30 moles per mole of the compound (VI). This reaction is carried out by heating a mixture of the compound (VI) and epichlorohydrin in the presence of sodium hydroxide at a temperature of 80° C. to 90° C. while stirring. The reaction product is recovered by evaporating excess epichlorohydrin off under reduced pressure and filtering off a by-produced sodium chloride.

The fluorine-containing epoxy compound having a large molecular weight, namely the epoxy resin of the present invention can be cured by a method for curing the conventional epoxy resin. For example, a curing agent is added to the epoxy resin and kept standing at a temperature of 5° to 200° C. for 10 minutes to 10 hours. Examples of the curing agent are aliphatic diamines (e.g. polymethylenediamine, polyetherdiamine, etc.), straight or branched aliphatic polyamines (e.g. diethylenetriamine, diethylaminopropylamine, animoethylerhanolamine, etc.), alicyclic polyamines (e.g. menthanediamine, isophoronediamine, N-aminoethylpiperazine, etc.), modified amines (e.g. adducts of ethylenetetramine), aromatic diamines (e.g. m-phenylenediamine, 4,4'-methylenedianiline, diaminodiphenylether, diaminodiphenylsulfone, etc.), secondary amines (e.g. N-methylpiperazine, piperazine, piperidine, etc.), tertiary amines (N,N'-dimethylpiperazine, triethanolamine, benzyldimethylamine, etc.), boron trifluoride-monomethylamine complex, low molecular weight compounds of melamine resin or sulfide resin, and anhydrides (e.g. phthalic anhydride, chlorendic anhydride, etc.). The curing agent is used in an amount of 0.1 to 10 equivalents, preferably 0.5 to 3 equivalents per equivalent of the epoxy groups in the fluorine-containing epoxy resin of the present invention.

Alternatively, the fluorine-containing epoxy resin of the present invention containing an initiator which generates a cationic species by irradiation of ultraviolet light can be cured by irradiation of ultraviolet light. Examples of such initiator are diazonium salts (e.g. p-methoxybenzenediazonium hexaflucrophosphate, p-chlorobenzenediazonium hexafluorophosphare, etc.), diaryliodonium salts (e.g. diphenyliodonium hexafluorophosphate, 4,4-di-tert.-butylphenyliodonium hexafluorophosphate, etc.) and triarylsulfonium salts (e.g. diphenyl-4-thiophenoxyphenyl sulfonium, etc.).

The fluorine-containing epoxy resin of the present invention has a large fluorine content and in turn good heat resistance, moisture resistance, tracking resistance and weather resistance. Thus, it is useful as an adhesive, a coating material, a molding material and the like. Particularly, it is used as an adhesive for bonding the optical parts such as the quartz optical fiber or the optical connector since its refractive index after cured is close to that of the quartz.

From the novel fluorine-containing aromatic compound (I), a novel fluorine-containing polyimide is prepared. It is represented by the formula:

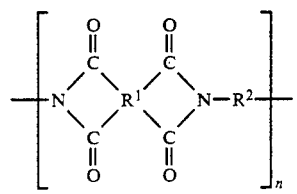

wherein R¹ is a residue which is formed by removing two acid anhydride groups from an aromatic tetracarboxylic anhydride, R² is a residue which is formed by removing two amino groups from an aromatic diamine provided that at least one of R¹ and R² contains a group of the formula:

wherein X and Y are the same as defined above, and n is an integer not smaller than 10.

One of the characteristics of the fluorine-containing polyimide of the present invention resides in that the group of the formula:

wherein X and Y are the same as defined above is present between two aromatic rings. Therefore, at least one of R¹ and R² should contain this group. That is, R¹ should be, for example, a group of the formula:

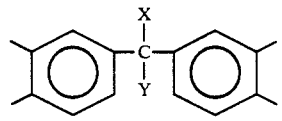

and/or R² should be, for example, a group of the formula:

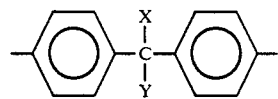

In addition to the above group, examples of R¹ includes:

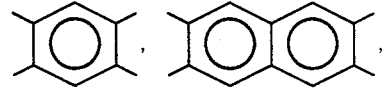

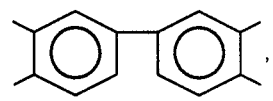

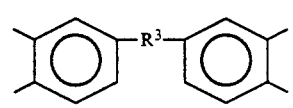

wherein R³ is —O—, —CO—, —SO₂—, —C(CH₃)₂—, —C(CF₃)₂—, —Si(CH₃)₂—,

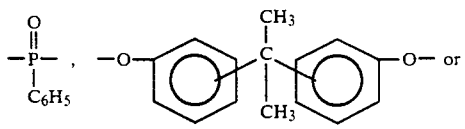

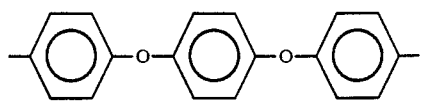

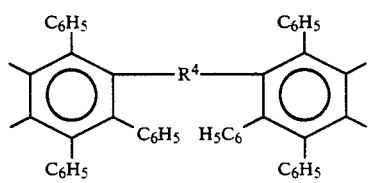

wherein R⁴ is —C₆H₄—, —C₆H₄O—C₆H₄— or —C₆H₄—O—C₆H₄—O—C₆H₄—,

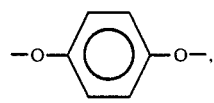

wherein R⁵ is —O—, —O—(CH₂)₄—O—, —O—(CH₂)₆—O—,

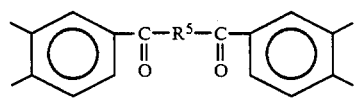

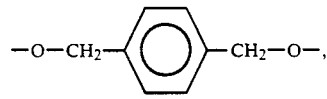

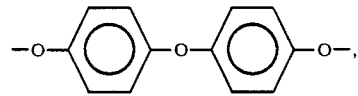

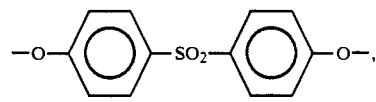

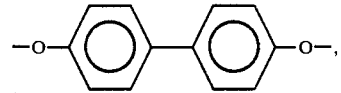

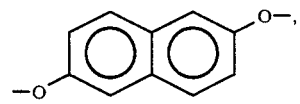

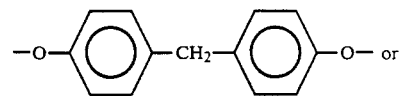

-continued

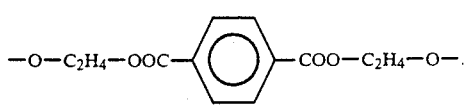

In addition to the above group, examples of $R^2$ include:

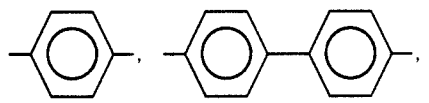

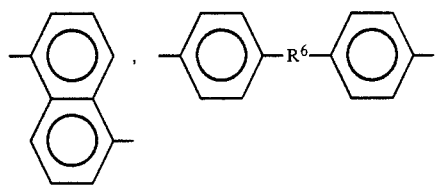

wherein $R^6$ is —O—, —CO—, —S—, —CH$_2$—, —(CH$_3$)$_2$, —C(CF$_3$)$_2$—, —SO$_2$—,

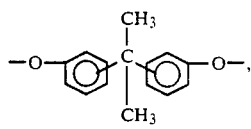

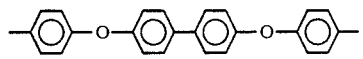

or —Si(CH$_3$)$_2$—, and

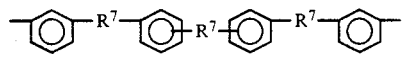

wherein $R^7$ is —O—, —SO$_2$—, —CH$_2$—, —CO—, —C(CH$_3$)$_2$— or —S—.

The fluorine-containing polyimide of the present invention may be prepared by reacting an aromatic diamine of the formula:

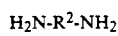

wherein $R^2$ is the same as defined above with an aromatic tetracarboxylic anhydride of the formula:

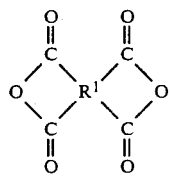

wherein $R^1$ is the same as defined above to obtain a polyamide acid of the formula:

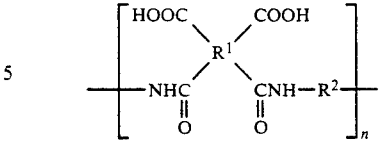

wherein $R^1$ and $R^2$ are the same as defined above, and n is an integer not smaller than 10, and then converting the polyamic acid to the polyimide.

In the combination of the aromatic diamine and the aromatic tetracarboxylic anhydride, when an aromatic diamine other than the diamine of the formula:

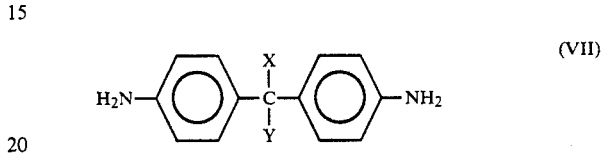

(VII)

wherein X and Y are the same as defined above is used, the aromatic tetracarboxylic anhydride should be one having the formula:

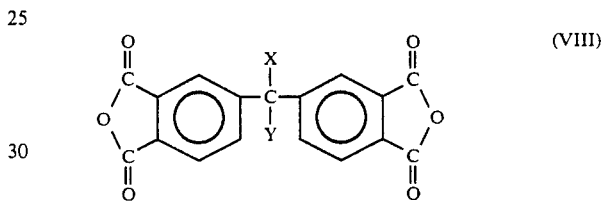

(VIII)

wherein X and Y are the same as defined above. When an aromatic tetracarboxylic anhydride other than the anhydride (VIII), the aromatic diamine (VII) should be used as the diamine element.

The aromatic diamine (VII) may be prepared by reacting the compound (II) with toluene in the presence of the Lewis acid to obtain a compound of the formula:

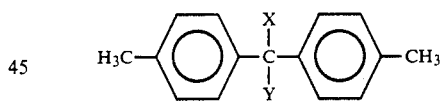

wherein X and Y are the same as defined above, oxidizing this compound and reacting the oxidized compound with hydrogen azide. The anhydride (VIII) may be prepared by reacting the compound (II) with o-xylene in the presence of the Lewis acid to obtain a compound of the formula:

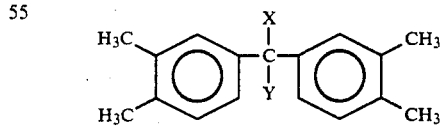

wherein X and Y are the same as defined above, oxidizing the resulting compound and then thermally dehydrating it.

Other examples of the aromatic diamine are 4,4'-diaminodiphenyl ether, 3,3'-diaminodiphenyl ether, 3,4'-diaminodiphenyl ether, 4,4'-diaminodiphenyl thioether, 3,3'-diaminodiphenyl thioether, 3,4'-diaminodiphenyl thioether, 4,4'-diaminobenzophenone, 3,3'-diaminobenzophenone, 3,4'-diaminobenzophenone, 4,4'-diaminodiphenylsulfone, 3,3'-diphenylsulfone, 3,4'-diphenylsulfone, 4,4'-diaminodiphenylmethane, 3,3'-diaminodiphenylmethane, 3,4'-diaminodiphenylmethane, 2,2'-bis(4-aminophenyl)propane, 2,2'-bis(3-aminophenyl)propane, benzidine, 3,3'-diaminobiphenyl, 3,4'-diaminobiphenyl, p-phenylenediamine, m-phenylenediamine, bis(4-amino)dimethylsilane, bis(4-aminophenyl)diethylsilane, bis(4-aminophenyl)diphenylsilane and the like.

Other examples of the aromatic tetracarboxylic anhydride are pyromelitic dianhydride, 2,3,6,7-naphthalene tetracarboxylic dianhydride, 3,3',4,4'-diphenyl tetracarboxylic dianhydride, 1,2,5,6-naphthalene tetracarboxylic dianhydride, 2,2',3,3'-diphenyl tetracarboxylic dianhydride, 2,3',3,4'-diphenyl tetracarboxylic dianhydride, 2,2'-bis(3,4-dicarboxyphenyl)propane dianhydride, bis(3,4-dicarboxy)phenyl sulfone dianhydride, 3,4,9,10-perylene tetracarboxylic dianhydride, bis(3,4-dicarboxyphenyl)ether dianhydride, catelene-1,4,5,8-tetracarboxylic dianhydride, 2,2-bis(2,3-dicarboxyphenyl)propane dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)methane dianhydride, bis(3.4-dicarboxyphenyl)-thioether dianhydride, 3,4,3',4'-benzophenone tetracarboxylic dianhydride, bis(3,4-dicarboxyphenyl)dimethylsilane dianhydride, bis(3,4-dicarboxyphenyl)diphenylsilane dianhydride and the like.

The aromatic anhydride and the aromatic diamine are reacted in an equimolar amount in the presence of a solvent while stirring. The reaction temperature is from 0° to 60° C., preferably from 20° to 40° C., and the reaction time is from 1 to 24 hours, preferably from 3 to 12 hours. Specific examples of the solvent are N-methyl-2-pyrolidone (NMP), dimethylacetoamide (DMAc), dimethylformamide (DMF), sulforan, tetrahydrofuran etc. When the aromatic diamine (VII) and the aromatic anhydride (VIII) are reacted, preferably used solvent are hologen-containing solvents such as tetrachlorohexafluorobutane, trichlorotrifluoroethane, tetrachlorodifluoroethane and perchloroethylene.

The polyamic acid can be converted to the polyimide by a per se conventional method. For example, the polyimide acid is easily converted to the polyimide by heating the former at a temperature not lower than 200° C., preferably from 230° to 400° C.

According to the present invention, the polyamic acid is coated on the semiconductor device and a lead wire and then heated to cure.

The present invention will be explained further in detail by the following Examples.

REFERENCE EXAMPLE

In a 5 l four-necked flask equipped with a reflux condenser, a thermometer, a nitrogen-introducing tube and a stirrer, metal magnesium (24.31 g, 1 mol), absolute diethyl ether (150 ml) and a small amount of iodine crystal were charged and stirred with introducing nitrogen. $C_8F_{17}CH_2CH_2I$ (574 g, 1 mol) dissolved in diethyl ether (600 ml) was dropwise added. After finishing the addition, a reaction solution was heated to reflux for 2 hours. After cooling the reaction solution to a room temperature, $CF_3CO_2CH_3$ (128 g, 1 mol) was dropwise added. Then the reaction solution was stirred for two hours.

After the reaction finished, an aqueous sulfric acid solution was added to acidify the reaction solution. A diethyl ether layer was washed with water three times, dried over anhydrous sodium sulfate and then with phosphorous pentoxide. The diethyl ether layer was distilled under reduced pressure to give a ketone compound, $C_8F_{17}CH_2CH_2COCF_3$. Yield: 174 g (32%). Boiling point: 96°-98° C./17 mmHg.

IR (NaCl): $\nu(cm^{-1})$ = 1,780, 1,250, 1,210, 1,150, 1,010

$^{19}F$-NMR ($CCl_4$) $\delta$(ppm): $-12.7$ (s, 3F), 35.9 (broad, 2F), 43.2 (broad, 6F), 44.0 (broad, 2F), 44.3 (broad, 2F), 47.5 (broad, 2F)

EXAMPLE 1

In a 300 ml autoclave, toluene (15.2 g, 0.165 mol), $C_8F_{17}CH_2CH_2COCF_3$ (40.9 g, 0.075 mol) obtained in Reference Example and hydrogen fluoride (40 ml) were charged and reacted at 90°-100° C. under 9 kg/cm² for 18 hours with stirring.

After the reaction finished, hydrogen fluoride was removed and a reaction product was extracted with trichlorotrifluoroethane. Trichlorotrifluoroethane was distilled off from an extract under a reduced pressure to give a compound of the formula:

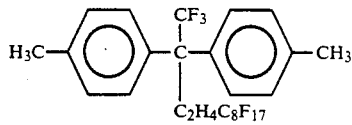

Yield: 38.9 g (73%).

IR (NaCl): $\nu(cm^{-1})$ = 2,900, 1,520, 1,465, 1,330, 1,240, 1,210, 1,150, 1,010, 815, 730, 710

$^1H$-NMR ($CCl_4$/TMS): $\delta$(ppm) = 1.5–3.3 (m, 4H), 2.30 (s, 6H), 7.05 (s, 8H)

$^{19}F$-NMR ($CCl_4$/TFA): $\delta$(ppm) = $-12.1$ (s, 3F), 2.8 (t, 3F), 36.3 (broad, 2F), 43.5 (broad, 6F), 44.4 (broad, 2F), 44.7 (broad, 2F), 47.9 (broad, 2F)

EXAMPLE 2

In a 100 ml autoclave, the compound (20.0 g, 0.028 mol) of the formula:

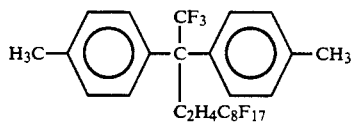

obtained in Example 1 and acetic acid (73 ml) were charged. Chromium (VI) oxide (18.3 g) was added to a reaction mixture with stirring at 80° C. The reaction mixture was stirred for 12 hours with keeping a temperature at 80°-90° C.

After the reaction finished, acetic acid was distilled off from the reaction mixture under a reduced pressure. An 5% aqueous sodium hydroxide solution (400 ml) was added to dissolve a residual solid. The solution was filtered to separate chromium (III) oxide. An aqueous sodium sulfate solution was added to the filtrate to precipitate a white solid, which was filtered and dried to give a compound of the formula:

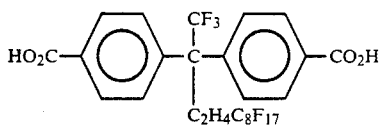

Yield, 18.5 g (86%).

IR (KBr): $\nu(cm^{-1})$=3,000, 1,700, 1,615, 1,425, 1,330, 1,285, 1,240, 1,200, 1,150, 1,120, 1,010, 855, 810, 780, 725, 710

$^1$H-NMR (DMSO-d$_6$/TMS): $\delta$(ppm)=1.6-3.1 (m, 4H), 7.57 (dd, J=8 Hz, 577 Hz, 8H), 9.5-10.5 (broad, 2H)

$^{19}$F-NMR (DMS$_0$-d$_6$/TFA): $\delta$(ppm)=−13.0 (s, 3F), 2.1 (t, 3F), 35.9 (broad, 2F), 43.0 (broad, 6F), 44.0 (broad, 2F), 44.3 (broad, 2F), 47.3 (broad, 2F)

EXAMPLE 3

In a 500 ml three-necked flask, the compound (15.0 g, 0.0195 mol) of the formula:

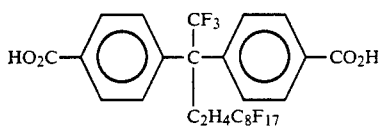

obtained in Example 2, concentrated sulfuric acid (63 g) and chloroform (200 ml) were charged. 1N hydrazoic acid (58.5 ml) was dropwise added to reflux for two hours with heating at 50° C.

After the reaction finished, the reaction solution was cooled to a room temperature and poured in water (400 ml) to make a precipitate. The precipitated was filtered, and an aqueous sodium hydroxide solution was added to make it alkaline. The mixture was extracted with chloroform (500 ml). The extract was evaporated to give a compound of the formula:

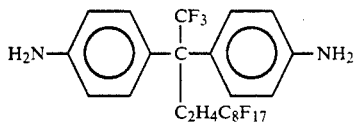

Yield, 8.34 g (60%).

IR (KBr): $\nu(cm^{-1})$=3,450, 3,370, 1,630, 1.520, 1,370, 1,335, 1,280, 1,250, 1,230, 1,200, 1,150, 1,110, 1,005, 960, 825, 820, 705

$^1$H-NMR (CDCl$_3$/TMS): $\delta$(ppm)=1.5-2.9 (m, 4H), 3.62 (s, 4H), 6.72 (dd, J=8 Hz, 37 Hz, 8H)

$^{19}$F-NMR (CDCl$_3$/TFA): $\delta$(ppm)=−12.2 (s, 3F), 2.1 (t, 3F), 35.7 (broad, 2F), 43.0 (broad, 6F), 44.0 (broad, 2F), 44.3 (broad, 2F), 44.3 (broad, 2F), 47.3 (broad, 2F)

EXAMPLE 4

In a 100 ml autoclave, o-xylene (17.1 g, 0.1617 mol), C$_8$F$_{17}$CH$_2$CH$_2$COCF$_3$ (40.0 g, 0.0735 mol) and hydrogen fluoride (37 ml) were charged and reacted at 90°-100° C. under 9 kg/cm$^2$ for 18 hours with stirring.

After the reaction finished, the resultant mixture was extracted with trichlorotrifluoroethane. Trichlorotrifluoroethane was distilled off from the extract under a reduced pressure to give a compound of the formula:

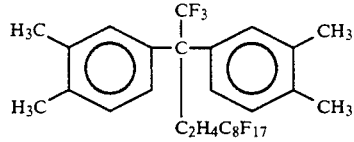

Yield, 38.3 g (70%).

IR (KBr): $\nu(cm^{-1})$=2,950, 1,510, 1,470, 1,450, 1,375, 1,330, 1,200, 1,145, 1,110, 1,020, 990, 965, 880, 820, 735, 710

$^1$H-NMR (CCl$_4$/TMS): $\delta$(ppm)=1.6-3.1 (m, 4H), 2.22 (s, 12H), 6.94 (s, 6H)

EXAMPLE 5

In a 500 ml autoclave, a compound (38.0 g, 0.05 mol) of the formula:

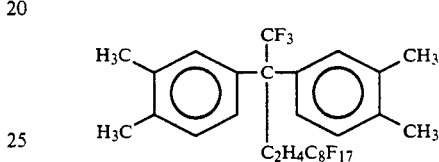

obtained in Example 4, 60% nitric acid (58 ml) and water (57 ml) were charged and reacted at 170°-180° C. for 2 hours.

After the reaction finished, a reaction mixture was filtered to separate a solid product. An 5% aqueous sodium hydroxide solution was added to the solid product to dissolve it and filtered. Aqueous sulfric acid solution was added to acidify the filtrate and extracted with ether. Ether was distilled off from the extract to give a compound of the formula:

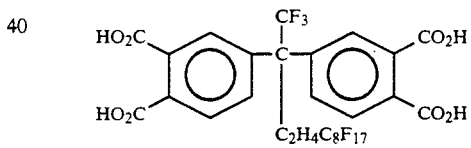

Yield: 39.7 g (90%).

IR (KBr): $\nu(cm^{-1})$=3,400, 3,000, 1,710, 1,615, 1,580, 1,510, 1,425, 1,210, 1,160, 1,110, 1,070, 1,020, 980, 820, 800, 725, 705

$^1$H-NMR (acetone-d$_6$/TMS): $\delta$(ppm)=1.7-3.3 (m, 4H), 6.6-7.6 (broad, 4H), 7.6-8.0 (m, 6H)

$^{19}$F-NMR (acetone-d$_6$/TFA): $\delta$(ppm)=−11.5 (s, 3F), 3.6 (t, 3F), 36.9 (broad, 2F), 44.3 (broad, 6F), 45.2 (broad, 2F), 45.5 (broad, 2F), 48.6 (broad, 2F)

EXAMPLE 6

In a 200 ml eggplant flask, the compound (39.7 g, 0.046 mol) of the formula:

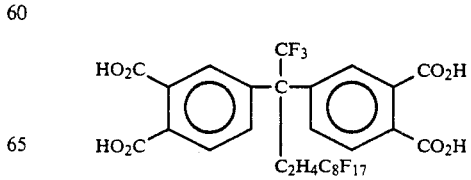

and heated at a temperature of 150°-160° C. for 6 hours.

Thereafter, the reaction product was removed from the eggplant flask and recrystallized from ether to give a white crystalline compound of the formula:

$$\text{(phthalic anhydride)}-\underset{\underset{C_2H_4C_8F_{17}}{|}}{\overset{CF_3}{\underset{|}{C}}}-\text{(phthalic anhydride)}$$

Yield: 22.7 g (60%).

IR (KBr): $\nu(cm^{-1}) = 1,860, 1,780, 1,620, 1,490, 1,470, 1,435, 1,400, 1,375, 1,335, 1,205, 1,180, 1,155, 1,120, 1,015, 900, 740, 725, 700$ $^1$H-NMR (hot CDCl$_3$/TMS): $\delta(ppm) = 1.6-3.2$ (m, 4H), 7.5-8.1 (m, 6H)

$^{19}$F-NMR (hot CDCl$_3$/TFA): $\delta(ppm) = -13.2$ (s, 3F), 2.1 (t, 3F), 35.8 (broad, 2F), 43.0 (broad, 6F), 44.0 (broad, 4F), 47.2 (broad, 2F)

EXAMPLE 7

In a 100 ml autoclave, phenol (15.2 g, 0.162 mol), C$_8$F$_{17}$CH$_2$CH$_2$COCF$_3$ (40.0 g, 0.0735 mol) obtained in Example 6 and hydrogen fluoride (37 ml) were charged and reacted at temperature of 85°-90° C. under pressure of 9 kg/cm$^2$ for 15 hours with stirring.

After the reaction finished, hydrogen fluoride was removed to give a yellow solid product (49.6 g). The product was recrystallized from tetrafluoropropanol to give a white crystalline product of the formula:

$$HO-\text{(phenyl)}-\underset{\underset{C_2H_4C_8F_{17}}{|}}{\overset{CF_3}{\underset{|}{C}}}-\text{(phenyl)}-OH$$

Yield: 31.8 g (70%).

IR (KBr): $\nu(cm^{-1}) = 3,350, 1,610, 1,600, 1,515, 1,460, 1,440, 1,350, 1,250, 1,210, 1,155, 1,110, 1,005, 830, 700$ $^1$H-NMR (acetone-d$_6$/TMS): $\delta(ppm) = -1.7-3.2$ (m, 4H), 6.95 (dd, J=8 Hz, 28 Hz, 8H), 8.35 (s, 2H)

$^{19}$F-NMR (acetone-d$_6$/TFA): $\delta(ppm) = -12.2$ (s, 3F), 2.2 (t, 3F), 35.9 (broad, 2F), 44.2 (broad, 6F), 44.3 (broad, 4F), 47.5 (broad, 2F)

EXAMPLE 8

In a 500 ml autoclave, phenol (20.6 g, 0.22 mol), C$_3$F$_7$OCF(CF$_3$)CH$_2$CH$_2$COCF$_3$ (41.0 g, 0.1 mol) obtained in Reference Example and hydrogen fluoride (50 g, 2.5 mol) were charged and reacted at temperature of 80°-84° C. for 15 hours with stirring.

After the reaction finished, the reaction solution was poured in an iced water. Hydrogen fluoride was removed by decantation to give a highly viscous liquid. The liquid was extracted with diethyl ether (300 ml) and the extract was neutralized with sodium hydrogen carbonate, and washed with water twice. Then, the extract was dried over sodium sulfate and ether was distilled off from the extract to give a compound of the formula:

$$HO-\text{(phenyl)}-\underset{\underset{CF_3}{|}}{\overset{CF_3}{\underset{\underset{C_2H_4CFOC_3F_7}{|}}{C}}}-\text{(phenyl)}-OH$$

Yield: 34.1 g (59%). Boiling point: 203°-205° C./1 mmHg.

IR (KBr): $\nu(cm^{-1}) = 3,360, 1,615, 1,605, 1,520, 1,440, 1,340, 1,305, 1,230, 1,200, 1,160, 1,090, 1,010, 975, 840, 750$ $^1$H-NMR (DMSO-d$_6$/TMS): $\delta(ppm) = 1.5-3.0$ (m, 4H), 6.82 (dd, J=8 Hz, 24 Hz, 8H), 9.42 (s, 2H)

$^{19}$F-NMR (DMSO-d$_6$/TFA): $\delta(ppm) = -12.2$ (s, 3F), 2.9 (m, 5F), 4.7 (d, 3F), 51.3 (m, 3F)

EXAMPLE 9

In a 500 ml autoclave, toluene (60.81 g, 0.66 mol), C$_4$F$_9$CH$_2$CH$_2$COCF$_3$ (103.23 g, 0.3 mol) and hydrogen fluoride (150 g) were charged and reacted at temperature of 85°-90° C. with stirring.

After the reaction finished, a reaction mixture was extracted with trichlorotrifluoroethane. Trichlorotrifluoroethane was distilled off from the extract to give a compound of the formula:

$$H_3C-\text{(phenyl)}-\underset{\underset{C_2H_4C_4F_9}{|}}{\overset{CF_3}{\underset{|}{C}}}-\text{(phenyl)}-CH_3$$

Yield: 127.7 g (83%).

IR (KBr): $\nu(cm^{-1}) = 3,000, 1,615, 1,520, 1,465, 1,350, 1,225, 1,135, 1,010, 920, 880, 850, 810, 730$ $^1$H-NMR (CDCl$_3$/TMS): $\delta(ppm) = 1.7-2.9$ (m, 4H), 2.35 (s, 6H), 7.17 (s, 8H)

$^{19}$F-NMR (CDCl$_3$): $\delta(ppm) = -12.3$ (s, 3F), 2.7 (t, 3F), 36.4 (m, 2F), 47.6 (t, 2F)

EXAMPLE 10

In a 100 ml autoclave, the compound (105.0 g, 0.206 mol) of the formula:

$$H_3C-\text{(phenyl)}-\underset{\underset{C_2H_4C_4F_9}{|}}{\overset{CF_3}{\underset{|}{C}}}-\text{(phenyl)}-CH_3$$

60% nitric acid (128 ml) and water (126 ml) were charged and reacted at temperature of 180°-190° C. with stirring.

After the reaction finished, a reaction product was filtered to separate a solid product. An 5% aqueous sodium hydroxide (400 ml) was added to the solid product, and undissolved materials were filtered off. An aqueous sulfric acid solution was added to acidify the filtrate to precipitate a white solid, which was separated by filtration and dried to give a compound of the formula:

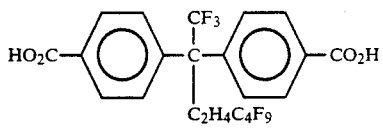

Yield: 112.4 g (96%).

IR (KBr): $\nu(cm^{-1})=3,000, 1,615, 1,520, 1,465, 1,350, 1,225, 1,135, 1,010, 920, 880, 850, 810, 730$ $^1$H-NMR (CDCl$_3$/TMS): $\delta$(ppm)=1.7–2.9 (m, 4H), 2.35 (s, 6H), 7.17 (s, 8H)

$^{19}$F-NMR (CDCl$_3$): $\delta$(ppm)=$-$12.3 (s, 3F), 2.7 (t, 3F), 36.4 (m, 2F), 45.7 (m, 2F), 47.6 (t, 2F)

EXAMPLE 11

In a 2 liter three-necked flask, the compound (64.0 g, 0.112 mol) of the formula:

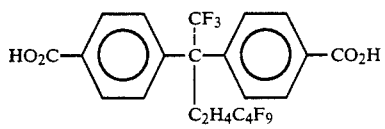

obtained in Example 10, concentrated nitric acid (176 g.) and chloroform (350 ml) were charged. Then 1.1N hydrazoic acid (306 ml) was dropwise added, and a mixture was heated to temperature of 40°–45° C. for 2 hours with stirring. After the mixture was stirred at a room temperature for 12 hours, a chloroform layer was separated from an aqueous layer. The aqueous layer was made alkaline with sodium hydroxide and extracted with chloroform (400 ml). After the extract was dried over sodium sulfate, chloroform was distilled off and the residue was recrystallized from petroleum benzinediethyl ether to give a compound of the formula:

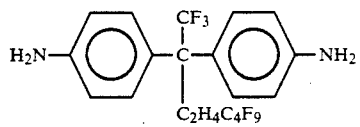

Yield: 32.8 g (54%).

IR (KBr): $\nu(cm^{-1})=3,420, 3,350, 1,620, 1,520, 1,460, 1,360, 1,320, 1,280, 1,250, 1,220, 1,200, 1,160, 1,130, 1,020, 1,005, 920, 850, 835, 720$ $^1$H-NMR (DMSO-d$_6$): $\delta$(ppm)=1.5–3.8 (m, 4H), 5.21 (s, 4H), 6.74 (dd, J=8 Hz, 36 Hz, 8H)

$^{19}$F-NMR (DMSO-d$_6$): $\delta$(ppm)=$-$12.6 (s, 3F), 2.4 (t, 3F), 35.9 (m, 2F), 45.8 (m, 2F), 47.5 (t, 2F)

EXAMPLE 12

In a 100 ml autoclave, o-xylene (63.0 g, 0.594 mol), C$_4$F$_9$CH$_2$CH$_2$COCF$_3$ (92.9 g, 0.27 mol) and hydrogen fluoride (135 g) were charged and reacted at a temperature of 75°–80° C. for 17 hours with stirring.

After the reaction finished, a reaction mixture was extracted with trichlorotrifluoroethane. Trichlorotrifluoroethane was distilled off from an extract to give a compound of the formula:

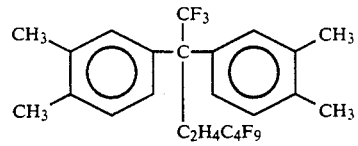

Yield 130.9 g (90%).

IR (NaCl): $\nu(cm^{-1})=2,950, 1,620, 1,575, 1,505, 1,450, 1,225, 1,130, 1,015, 990, 900, 880, 810, 740, 730, 725, 720, 700$ $^1$H-NMR (CCl$_4$): $\delta$(ppm)=1.6–3.9 (m, 4H), 2.23 (s, 12H), 7.00 (s, 6H)

$^{19}$F-NMR (CCl$_4$): $\delta$(ppm)=$-$12.4 (s, 3F), 2.9 (t, 3F), 36.6 (m, 2F), 45.9 (m, 2F), 47.9 (t, 3F)

EXAMPLE 13

In a 500 ml autoclave, the compound (80.8 g, 0.15 mol) of the formula:

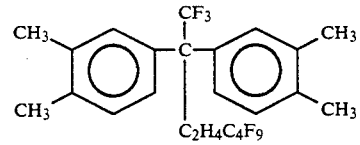

obtained in Example 12, 60% nitric acid (166 ml) and water (164 ml) were charged and reacted at temperature of 170°–180° C. for 2 hours with stirring.

After the reaction finished, a reaction product was filtered. An 5% aqueous sodium hydroxide solution was add to dissolve a filtered solid and filtered. An aqueous sulfric acid was added to acidify the filtrate and extracted with ether. The extract was distilled to remove ether to give a compound of the formula:

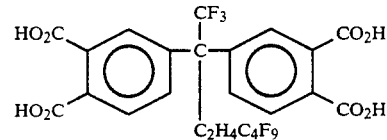

Yield: 80.9 g (88%).

IR (KBr): $\nu(cm^{-1})=3,000, 1,705, 1,605, 1,570, 1,500, 1,420, 1,230, 1,160, 1,130, 1,070, 1,010, 880, 850, 800, 720$ $^1$H-NMR (DMSO-d$_6$) $\delta$(ppm)=1.8–3.8 (m, 4H), 7.3–7.8 (m, 6H), 10–12 (broad, 4H)

$^{19}$F-NMR (DMSO-d$_6$): $\delta$(ppm)=$-$13.2 (s, 3F), 2.1 (t, 3F), 35.3 (m, 2F), 45.4 (m, 2F), 47.2 (t, 2F)

EXAMPLE 14

In a 200 ml eggplant flask, the compound (86.9 g, 0.132 mol) of the formula:

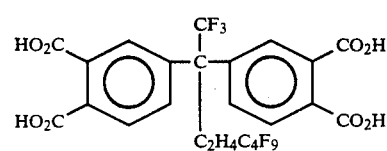

obtained in Example 13 was charged and heated at 160° C. under a reduced pressure for 5 hours.

After heating, a product was removed and recrystallized from ether to give a white crystalline product of the formula:

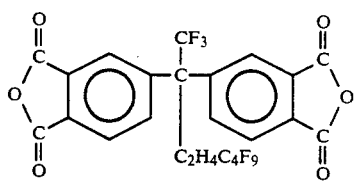

Yield: 60.6 g (65%).

IR (KBr): $\nu(cm^{-1})$ = 1,860, 1,785, 1,620, 1,430, 1,330, 1,255, 1,235, 1,175, 1,150, 1,130, 1,115, 1,010, 900, 850, 740, 720, 700

$^1$H-NMR (DMSO-d$_6$): $\delta$(ppm) = 1.5-3.6 (m, 4H), 7.7-8.2 (m, 6H)

$^{19}$F-NMR (DMSO-d$_6$): $\delta$(ppm) = -13.3 (s, 3F), 2.3 (t, 3F), 35.2 (m, 2F), 45.2 (m, 2F), 47.3 (t, 2F)

EXAMPLE 15

In a 3 l round bottom flask equipped with a thermometer, a stirrer and a reflux condenser, a compound (600 g, 0.840 mol) of the formula:

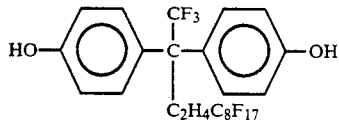

epichlorohydrin (1166 g, 12.60 mol), pure water (4 ml) and sodium hydroxide (3 g) were charged and heated to 83°-87° C. with stirring until sodium hydroxide solid disappeared. Sodium hydroxide (5 g each) was added repeatedly with keeping a temperature at 83°-87° C. so that a total amount of sodium hydroxide was 70 g (1.75 mol). After addition of sodium hydroxide and an exothermic reaction finished, a reaction mixture was stirred for one hour with keeping the temperature at 83°-87° C.

After the reaction finished, the reaction solution was distilled under a reduced pressure to remove unreacted epichlorohydrin, and a residue was cooled to 70° C. Benzene (100 ml) was added and filtered to separate off by-producted sodium chloride. A filtrate was distilled under reduced pressure to remove benzene and to give a liquid epoxy resin of the formula:

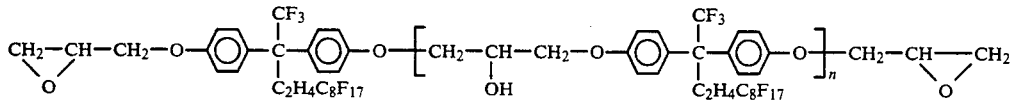

wherein an average of n is 0.2. Yield: 652 g. A value of n was determined by means of HPLC (High Performance Liquid Chromatography).

IR (NaCl): $\nu(cm^{-1})$ = 3,000, 1,615, 1,585, 1,520, 1,460, 1,260-1,100, 1,030, 1,000, 970, 915, 860, 830, 770, 740, 725, 710

$^1$H-NMR (CCl$_4$): $\delta$(ppm) = 6.86 (dd, 9.6H, J = 9 Hz, 27 Hz), 4.2-3.7 (m, 4.2H), 3.3-3.0 (m, 2.2H), 2.9-2.3 (m, 7.2H), 2.3-1.5 (broad, 2.4H)

$^{19}$F-NMR (CCl$_4$): $\delta$(ppm) = -12.1 (s, 3F), 2.3 (t, 3F), 35.9 (b, 2F), 43.2 (b, 6F), 44.3 (b, 4F), 47.5 (b, 2F)

EXAMPLE 16

In a 100 ml flask equipped with a thermometer, a stirrer and a reflux condenser, a compound (14.51 g, 0.025 mol) of the formula:

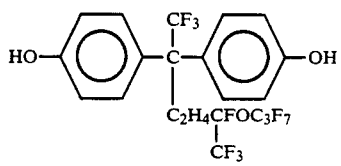

epichlorohydrin (34.70 g, 0.375 mol) and pure water (0.13 g) were charged and heated to 80°-85° C. Then sodium hydroxide (0.65 g each) was added twice with keeping a temperature at 70°-75° C. A total amount of sodium hydroxide was 2.05 g (0.051 mol). A reaction mixture was stirred for one hour with keeping the temperature at 80°-85° C.

After the reaction finished, the reaction solution was distilled under a reduced pressure to remove unreacted epichlorohydrin. Benzene (15 ml) was added to the residue and filtered to separate off by-producted sodium chloride. The filtrate was distilled under a reduced pressure to remove benzene and to give a liquid epoxy resin of the formula:

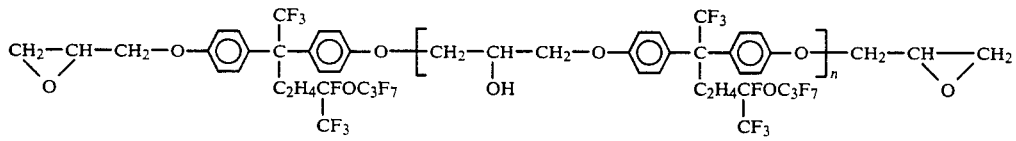

wherein an average of n is 0.2. Yield: 16.89 g.

IR (NaCl): $\nu(cm^{-1})$ = 2,900, 1,610, 1,580, 1,515, 1,460, 1,330, 1,290, 1,240, 1,200, 1,150, 1,080, 1,030, 1,010, 910, 830, 750

$^1$H-NMR (CCl$_4$): $\delta$(ppm) = 6.85 (dd, 9.6H, J = 9 Hz, 26 Hz), 4.2-3.7 (m, 4.2H), 3.3-3.0 (m, 2.4H), 2.9-2.3 (m, 7.2H), 2.2-1.7 (broad, 2.4H)

$^{19}$F-NMR (CCl$_4$): $\delta$(ppm) = -12.1 (s, 3F), 2.6 (m, 5F), 4.4 (d, 3F), 51.0 (s, 3F)

Experiment

The following properties (1) to (3) of the fluorine-containing epoxy resins obtained in Examples 15 and 16 and those of a fluorine containing epoxy resin (Comparative Example 1) of the formula:

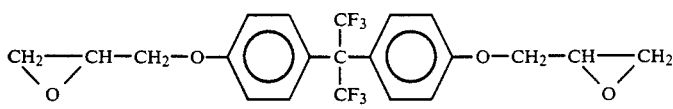

were measured. The resins were cured under the following conditions:

Curing agent: Epomic Q-694 (manufactured by Mitsui Petrochemical Industries, Ltd.)

Ratios of the curing agent:

5 parts by weight of the curing agent per 32 parts by weight of the resin of Example 15

10 parts by weight of the curing agent per 47 parts by weight of the resin of Example 16

4 parts by weight of the curing agent per 11 parts by weight of the resin of Comparative Example 1

Curing temperature: 65° C.

Curing time: 6 hours

The following properties were measured as follows:

(1) Refractive index

The refractive index is measured at 23° C. by an Abbe's refractometer.

(2) Glass transition temperature (Tg)

(3) Shearing adhesion strength

This is measured according to JIS K-6850 by using SUS-304.

Results of the properties (1) to (3) are shown in Table 1.

TABLE 1

| Resin | Refractive Index ($n_D^{23}$) | | Tg (°C.) | Shearing strength (kg/cm$^2$) |
|---|---|---|---|---|
| | Before curing | After curing | | |
| Ex. 15 | 1.448 | 1.462 | 76 | 128 |
| Ex. 16 | 1.461 | 1.481 | 56 | 120 |
| Comp. 1 | 1.497 | 1.527 | 76 | 125 |

The results of Table 1 show that the fluorine-containing epoxy resins of the present invention have lower refractive indexes than the conventional fluorine-containing epoxy resin and nearly the same as the refractive index of quartz ($n_D^{23} = 1.46$).

EXAMPLE 17

An aromatic diamine (14.25 g, 0.02 mol) of the formula:

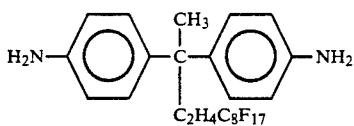

was dissolved in a mixed solvent of dimethylacetamide (35.0 g) and tetrachlorohexafluorobutane (65.0 g). Then, a powdery acid anhydride (16.45 g, 0.02 mol) of the formula:

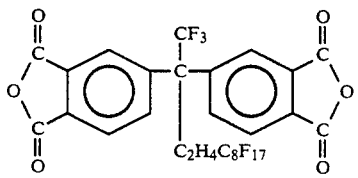

was added and reacted at 25° C. for 12 hours with stirring. A mixture containing a polyamic acid in a concentration of 23.5% by weight and having viscosity of 14,000 cps (23° C.) was produced. The polyamic acid mixture was coated on a glass plate and dried in an oven at 80° C. for 20 minutes and at 100° C., 200° C. and 300° C. respectively for 1 hour to give a polyimide film.

An infrared spectrum of the polyimide film was measured. Absorption due to C=O stretching vibration of an imide group was observed at 1,785 cm$^{-1}$ and 1,720 cm$^{-1}$.

The following properties of the polyimide film were measured:

(1) Water Absorption

A piece of the polyimide film (76.2 mm × 25.4 mm) is prepared and dried at 50° ± 3° C. for 24 hours. Then it is cooled in a desiccator and weighed ($W_1$). The piece is immersed in distilled water at 23° ± 1° C. for 24 hours, removed from the water, wiped with a cloth and weighed ($W_2$). The water absorption A is calculated according to the following equation:

$$A\ (\%) = \frac{W_2 - W_1}{W_1} \times 100$$

(2) Glass transition temperature ($T_g$)

A temperature at which the endothermic behavior begins is measured at a temperature raising rate of 10° C./min by using a DSC II type differential scanning calorimeter (manufactured by Perkin-Elmer Co.).

(3) Thermal Decomposition Temperature ($T_d$)

A temperature at which a weight decrease begins is measured at a temperature raising rate of 10° C./min by using a differential thermogravimetric analyzer DT-30 (manufactured by Shimadzu Corp.).

Results of the properties measured are shown in Table 2.

EXAMPLE 18

An aromatic diamine (10.25 g, 0.02 mol) of the formula:

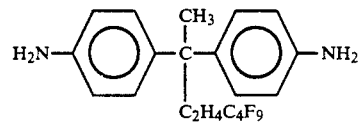

was reacted with an acid anhydride (12.45 g, 0.02 mol) of the formula:

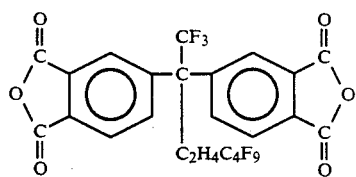

in the manner as in Example 17 to give a mixture containing a polyamic acid in a concentration of 20.1% by weight and having viscosity of 11,000 cps.

Then, a polyimide film was prepared and its properties were measured in the same manner as in Example 17. Results are shown in Table 2.

EXAMPLE 19

An aromatic diamine (7.12 g, 0.01 mol) of the formula:

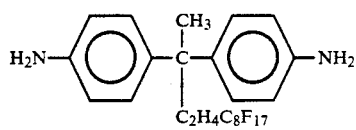

was dissolved in dimethylacetamide 30.0 g). Then powder of pyromellitic anhydride (2.18 g, 0.01 mol) was added and reacted in the same manner as in Example 17 to give a mixture containing polyamic acid in a concentration of 23.7% by weight and having viscosity of 9,000 cps.

Then, a polyimide film was prepared and its properties were measured in the same manner as in Example 17. Results are shown in Table 2.

EXAMPLE 20

Diaminodiphenyl ether (4.00 g, 0.02 mol) was dissolved in N-methyl-2-pyrrolidone (60 g). Powder of an acid anhydride (12.45 g, 0.02 mol) of the formula:

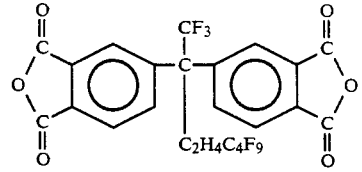

was added and reacted in the same manner as in Example 17 to give a mixture containing a polyamic acid in a concentration of 21.5% by weight and having viscosity of 12,000 cps.

Then, a polyimide film was prepared and its properties were measured in the same manner as in Example 17. Results are shown in Table 2.

Comparative Example 2

An aromatic diamine (1.333 g, 3 mmol) of the formula:

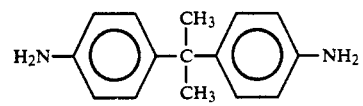

was dissolved in dimethylacetamide (20.0 g). An acid anhydride (1.003 g, 3 mmol) of the formula:

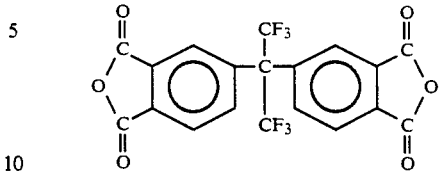

was added and reacted in the same manner as in Example 17 to give a mixture containing a polyamic acid in a concentration of 10.5% by weight.

Then, a polyimide film was prepared and its properties were measured in the same manner as in Example 17. Results are shown in Table 2.

Comparative Example 3

A polyimide having structure unit of the formula:

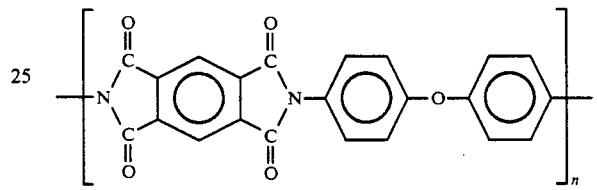

(KAPTON H manufactured by Du Pont) was used to prepare a film, and properties were measured as in the same manner as in Example 17. Results are shown in Table 2.

TABLE 2

| | Water absorption (%) | $T_g$ (°C.) | $T_d$ (°C.) | IR (cm$^{-1}$) |
|---|---|---|---|---|
| Ex. 17 | 0 | 183 | 428 | 1785, 1720 |
| Ex. 18 | 0 | 219 | 430 | 1785, 1730 |
| Ex. 19 | 0.1 | 231 | 424 | 1780, 1730 |
| Ex. 20 | 0.3 | 249 | 425 | 1785, 1720 |
| Comp. 2 | 0.6 | 310 | 464 | — |
| Comp. 3 | 2.9 | — | 546 | — |

Examples 21 to 24 and Comparative Example 4

In a four-necked flask equipped with a thermometer, a stirrer and a nitrogen-introducing tube, a purified diamine (0.1 mol) shown in Table 3 was charged followed by the addition of a solvent shown in Table 3 to dissolve the amine. Then, a tetracarboxylic dianhydride (0.1 mol) shown in Table 3 was added by portions with stirring. A reaction temperature was kept at 25°±2° C. After the addition of tetracarboxylic dianhydride was completed and a homogeneous solution was formed, the solvent was further added so as to adjust a solid content in the reaction mixture to 15% by weight. Then, the reaction mixture was kept at 25°±2° C. in a nitrogen atmosphere and stirred for 24 hours to give a polyamic acid solution.

The polyamic acid was dropped on an element and lead wires of 256 K bit LSI for D-RAM memory (16 pins), and heated at 80° C., 100° C., 150° C. and 200° C. respectively for one hour, and at 250° C. for 20 minutes to prepare a coating film of a fluorine-containing polyimide on the element and lead wires. The polyimide film had a thickness of 20 to 60 μm. The resultant element was sealed with an epoxy resin composition prepared as described hereinafter by a transfer molding (180° C., 1.5 minutes, 75 kg/cm²). Then it was postcured at 185° C. for 5 hours to give a semiconductor device sealed with the resin. One hundred LSI devices of each Example were used to determine moisture resistant reliability by a pressure cocker tester. Results are shown in Table 4. The moisture resistant reliability is expressed in terms of the number of sealed devices which default by corrosion of aluminum wiring when the sealed devices are positioned in a steam atmosphere at 120° C. under 2 atm.

Durez Co. Ltd, hydroxyl group equivalent: 105) (50 parts by weight), 2-phenyl imidazole (2 parts by weight) γ-glycidoxypropyl trimethoxysilane (2 parts by weight), fumed silica powder (350 parts by weight) and carbon black (1 parts by weight) was kneaded at 75°–90° C. by a twin-roll mill, cooled and ground in a flaker to prepare an epoxy resin composition for sealing.

What is claimed is:

1. A fluorine-containing aromatic compound of the formula:

TABLE 3

| | Diamine | Tetracarboxylic dianhydride | Solvent* |
|---|---|---|---|
| Ex. 21 | H₂N–⌬–C(CF₃)(C₂H₄C₈F₁₇)–⌬–NH₂ | dianhydride with CF₃ and C₂H₄C₈F₁₇ | NMP/S-316 (40/60 wt/wt) |
| Ex. 22 | H₂N–⌬–NH₂ | dianhydride with CF₃ and C₂H₄C₈F₁₇ | NMP/S-316 (80/20 wt/wt) |
| Ex. 23 | H₂N–⌬–O–⌬–NH₂ | dianhydride with CF₃ and C₂H₄C₈F₁₇ | NMP |
| EX. 24 | H₂N–⌬–C(CF₃)(C₂H₄C₄F₉)–⌬–NH₂ | pyromellitic dianhydride | NMP |
| Comp. 4 | H₂N–⌬–C(CF₃)(CF₃)–⌬–NH₂ | dianhydride with CF₃ and CF₃ | Dimethyl-acetamide |

(Note)*
NMP: N-Methyl pyrrolidone
S-316: A fluorine-containing solvent manufactured by Daikin Industries Ltd.

TABLE 4

| | Time (hours) | | | | |
|---|---|---|---|---|---|
| | 500 | 1000 | 1500 | 2000 | 2500 |
| Ex. 21 | 0 | 0 | 0 | 0 | 8 |
| Ex. 22 | 0 | 0 | 0 | 6 | 19 |
| Ex. 23 | 0 | 0 | 0 | 8 | 21 |
| Ex. 24 | 0 | 0 | 2 | 15 | 28 |
| Comp. 4 | 0 | 3 | 11 | 25 | 42 |

Preparation of Epoxy Resin Composition For Sealing

With an o-cresol novolac epoxy resin (EOCN-1025 manufactured by Nippon Kayaku Co. Ltd., epoxy equivalent: 2000) (100 parts by weight), a mixture of phenol novolac (PR-53194 manufactured by Sumitomo

wherein X is

in which $R_f$ is a perfluoroalkyl group having 1 to 10 carbon atoms, $R_f'$ is a perfluoroalkyl group having 1 to 12 carbon atoms, p is an integer of 1 to 3, q is an integer of 0 to 3, r is 0 or 1, s is an integer of 0 to 5 and t is an integer of 0 to 5, Y is X, a hydrogen atom, an alkyl group having 1 to 8 carbon atoms or a fluoroalkyl group having 1 to 8 carbon atoms, and each A is independently

in which D is an amino, carboxyl, hydroxyl, methyl or haloformyl group and n is integer of 1 or 2, or

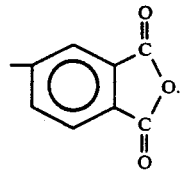

2. A fluorine-containing aromatic compound of the formula selected from the group consisting of

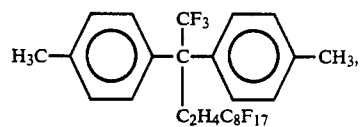

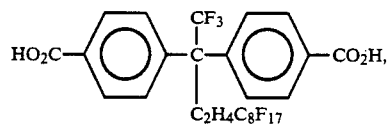

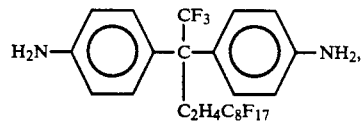

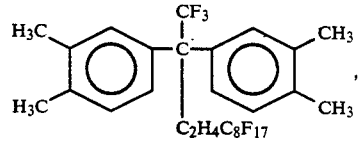

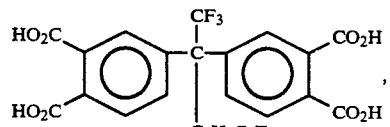

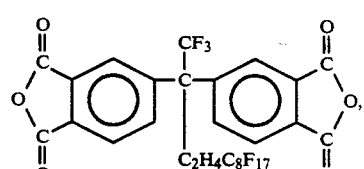

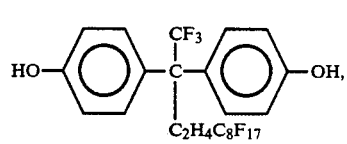

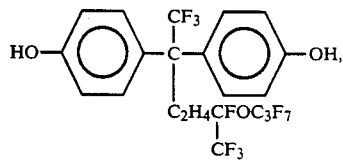

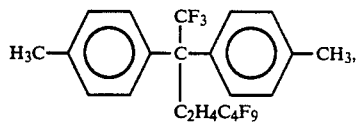

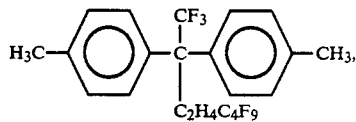

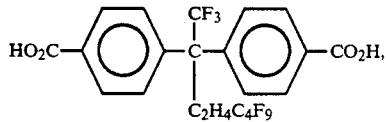

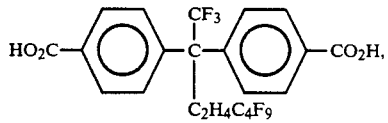

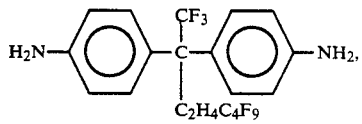

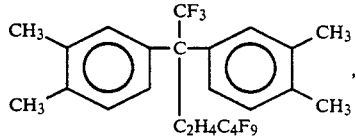

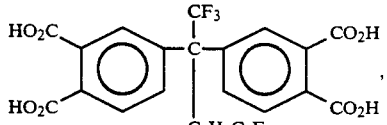

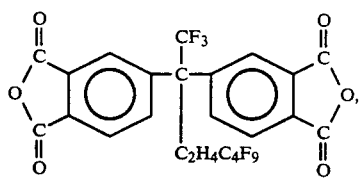

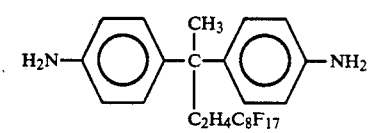

and

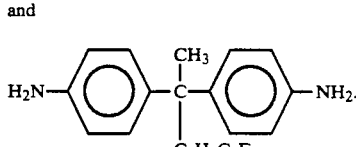

* * * * *

UNITED STATES PATENT AND TRADEMARK OFFICE
CERTIFICATE OF CORRECTION

PATENT NO. : 5,166,365
DATED : November 24, 1992
INVENTOR(S) : Yohnosuke Ohsaka, Tsutomu Kobayashi, Motonobu Kubo It is certified that error appears in the above-indentified patent and that said Letters Patent is hereby corrected as shown below:

On the title page: Item [75] Inventor: line 2, change "Kobayashhi" to --Kobayashi--.

Signed and Sealed this

Twelfth Day of April, 1994

*Attest:*

BRUCE LEHMAN

*Attesting Officer*     *Commissioner of Patents and Trademarks*